(12) United States Patent
Kim et al.

(10) Patent No.: US 10,675,161 B2
(45) Date of Patent: Jun. 9, 2020

(54) JOINT ASSEMBLY AND MOTION ASSISTANCE APPARATUS INCLUDING THE SAME

(71) Applicants: Samsung Electronics Co., Ltd., Suwon-si, Gyeonggi-do (KR); Korea University of Technology and Education, Cheonan-si, Chungcheongnam-do (KR)

(72) Inventors: Jeonghun Kim, Hwaseong-si (KR); Yong-Jae Kim, Cheonan-si (KR); Hyeong Seok Jeon, Cheongju-si (KR)

(73) Assignees: Samsung Electronics Co., Ltd., Gyeonggi-do (KR); Korea University of Technology and Education Industry-University Cooperation Foundation, Chungcheongnam-do (KR)

(\*) Notice: Subject to any disclaimer, the term of this patent is extended or adjusted under 35 U.S.C. 154(b) by 834 days.

(21) Appl. No.: 15/186,818

(22) Filed: Jun. 20, 2016

(65) Prior Publication Data
US 2017/0165087 A1    Jun. 15, 2017

(30) Foreign Application Priority Data

Dec. 15, 2015  (KR) .......................... 10-2015-0179230

(51) Int. Cl.
*A61H 1/02* (2006.01)
*A61F 2/66* (2006.01)
(Continued)

(52) U.S. Cl.
CPC .......... *A61F 2/6607* (2013.01); *A61F 5/0127* (2013.01); *A61H 1/0266* (2013.01);
(Continued)

(58) Field of Classification Search
CPC .................. A61F 2/6607; A61F 5/0127; A61F 2005/0139; A61F 5/0123;
(Continued)

(56) References Cited

U.S. PATENT DOCUMENTS 5,178,137 A  1/1993  Goor et al.
5,213,094 A  5/1993  Bonutti
(Continued)

FOREIGN PATENT DOCUMENTS

CN  1676112 A  10/2005
CN  103040594 A  4/2013
(Continued)

OTHER PUBLICATIONS

Extended European Search Report issued by the European Patent Office dated Nov. 23, 2017 for corresponding EP Patent Application No. 16203412.8.
(Continued)

*Primary Examiner* — Thomas Sweet
*Assistant Examiner* — Rebecca Lynee Zimmerman
(74) *Attorney, Agent, or Firm* — Harness, Dickey and Pierce, P.L.C.

(57) ABSTRACT

A joint assembly including a plurality of frames, each including contactors provided in opposite directions to each other and a middle portion configured to connect the contactors, and a connecting member configured to maintain a state in which contactors of two neighboring frames among the plurality of frames are in contact with each other is disclosed.

30 Claims, 14 Drawing Sheets

(51) Int. Cl.
 *A61F 5/01* (2006.01)
 *A61H 3/00* (2006.01)
 *A61F 2/50* (2006.01)

(52) U.S. Cl.
 CPC ........ *A61H 3/00* (2013.01); *A61F 2002/5007* (2013.01); *A61F 2005/0139* (2013.01); *A61F 2005/0141* (2013.01); *A61F 2005/0155* (2013.01); *A61H 2201/0107* (2013.01); *A61H 2201/164* (2013.01); *A61H 2201/165* (2013.01); *A61H 2201/1676* (2013.01)

(58) Field of Classification Search
 CPC ...... A61F 2005/0151; A61F 2005/0146; B25J 9/0006; A61H 3/00; A61H 2002/5007; A61H 2005/0141; A61H 2005/0155; A61H 2201/0107; A61H 2201/0164; A61H 2201/165; A61H 2201/1676; A61H 1/0266
 See application file for complete search history.

(56) References Cited

U.S. PATENT DOCUMENTS

| | | |
|---|---|---|
| 6,171,272 B1 | 1/2001 | Akita et al. |
| 8,808,214 B2 | 8/2014 | Herr et al. |
| 2003/0000198 A1 | 1/2003 | Hermey et al. |
| 2010/0268137 A1* | 10/2010 | Bachmann ............ A61F 5/0102 602/16 |
| 2012/0220831 A1* | 8/2012 | Cooper ............ A61B 17/00234 600/142 |
| 2013/0046218 A1 | 2/2013 | Wiggin et al. |
| 2015/0060560 A1 | 3/2015 | Yu et al. |
| 2015/0182366 A1 | 7/2015 | Takenaka et al. |
| 2017/0209330 A1* | 7/2017 | Hughes .................... B25J 17/00 |

FOREIGN PATENT DOCUMENTS

| | | |
|---|---|---|
| JP | 3002320 U | 7/1994 |
| JP | 2007-089633 A | 4/2007 |
| KR | 20110083782 A | 7/2011 |
| WO | WO-2006/039646 A2 | 4/2006 |

OTHER PUBLICATIONS

Partial European Search Report issued by the European Patent Office dated May 11, 2017 for corresponding EP Patent Application No. 16203412.8.

Chinese Office Action dated Oct. 21, 2019 for the corresponding CN patent application No. 201610702373.2 and translation thereof.

* cited by examiner

JOINT ASSEMBLY AND MOTION ASSISTANCE APPARATUS INCLUDING THE SAME

CROSS-REFERENCE TO RELATED APPLICATION

This application claims under 35 U.S.C. § 119 to Korean Patent Application No. 10-2015-0179230, filed on Dec. 15, 2015, in the Korean Intellectual Property Office, the entire contents of which are incorporated herein by reference in its entirety.

BACKGROUND

1. Field

At least one example embodiment relates to a joint assembly and/or a motion assistance apparatus including the joint assembly.

2. Description of the Related Art

With the onset of rapidly aging societies, many people may experience inconvenience and pain from joint problems, and interest in motion assistance apparatuses enabling the elderly or patients with joint problems to walk with less effort, may increase. Furthermore, motion assistance apparatuses for intensifying muscular strength of human bodies may be useful for military purposes.

In general, motion assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and femoral frames may be connected rotatably by hip joint portions, the femoral frames and sural frames may be connected rotatably by knee joint portions, and the sural frames and pedial frames may be connected rotatably by ankle joint portions.

The motion assistance apparatuses may include active joint structures including hydraulic systems and driving motors to drive joint portions to improve muscular strength of the legs of the users. For example, separate motors to transmit driving power may be provided at left and right hip joint portions, respectively.

SUMMARY

Some example embodiments relate to a joint assembly.

In some example embodiments, the joint assembly includes a plurality of frames each including contactors provided in opposite directions to each other and a middle portion configured to connect the contactors; and a connecting member configured to maintain contact between the contactors of two neighboring frames among the plurality of frames.

In some example embodiments, the contactors associated with a respective one of the plurality of frames face each other with the middle portion of the respective one of the plurality of frames therebetween.

In some example embodiments, the middle portion includes two symmetrically shaped legs extending in a U shape.

In some example embodiments, the contactors include contacting faces, and the two neighboring frames are in contact via the contacting faces.

In some example embodiments, the contacting faces include a plurality of gear teeth therein.

In some example embodiments, the gear teeth associated with the contacting faces of the two neighboring frames are configured to engage with each other.

In some example embodiments, each of the contactors includes a first contactor integral with the middle portion; second contactors on both ends of the first contactor; and an insertion member between the first contactor and each of the second contractors.

In some example embodiments, each of the first contactor and the second contactors has an outer side face and an inner side face, and the outer side face includes a plurality of gear teeth therein.

In some example embodiments, the insertion member comprises: a plurality of insertion bodies; and a wire configured to connect the insertion bodies along the middle portion of a respective one of the plurality of frames.

In some example embodiments, each of the insertion bodies is configured to contact the inner side of the first contactor and the inner side of the second contactor.

In some example embodiments, each of the first contactor and the second contactor includes a groove to accept a respective one of the insertion bodies.

In some example embodiments, the insertion bodies are configured to longitudinally slide in the groove of a respective one of the contactors.

In some example embodiments, each of the contactors has the groove therein such that a depth of the groove is maximize at a center of a respective one of the contactors and decreases toward ends of the respective one of the contactors.

In some example embodiments, when at least one frame of the plurality of frames moves, the at least one frame is configured to move a first one of the plurality of insertion bodies in a first direction and the wire is configured to move a second one of the plurality of insertion bodies in a second direction opposite the first direction.

In some example embodiments, each of the contactors further comprises: a hinge configured to movably connect the second contactors to the middle portion.

In some example embodiments, the connecting member further comprises: a side strip configured to pass through the contactors of each of the plurality of frames; and a middle strip configured to pass through the middle portion of each of the plurality of frames.

In some example embodiments, the plurality of frames are configured to align with each other in a longitudinal direction with respect to the connecting member.

In some example embodiments, the connecting member includes an elastic material configured to provide a restoring force to force the plurality of frames back toward in an initial state when the plurality of frames is out of the initial state.

In some example embodiments, the joint assembly further includes a cover frame on top of the plurality of frames and having a contacting face on a bottom thereof; and a bottom frame below the plurality of frames and having a contacting face on a top thereof.

Some example embodiments relate to a motion assistance apparatus.

In some example embodiments, the motion assistance apparatus includes a fixing device attached to a user; a support configured to move relative to the fixing device; a power transmitting device configured to transmit power to the support; and a joint assembly including a plurality of frames each including, a middle portion configured to cover a portion of a user and contactors disposed on both ends of the middle portion, and a connecting member configured to arrange the plurality of frames in a row to connect the fixing device and the support.

In some example embodiments, the connecting member includes: a side strip configured to pass through the contactors of each of the plurality of frames, the side strip including an elastic material configured to provide pressure to the plurality of frames such that the plurality of frames is in close contact with one another; and a middle strip configured to pass through the middle portion of each of the plurality of frames, the middle strip being a wire connected to the power transmitting device.

In some example embodiments, the contactors include a plurality of gear teeth such that the gear teeth of the contactors of two neighboring frames among the plurality of frames are configured to engage with each other.

In some example embodiments, the joint assembly further includes a cover frame on top of the plurality of frames and a bottom frame below the plurality of frames, and each of the contactors further includes, a first contactor connected to the middle portion; a second contactor movably connected to the first contactor via a hinge; and an insertion member between the first contactor and the second contractor.

In some example embodiments, the insertion member includes: a plurality of insertion bodies each configured to be insert into the first contactor and the second contactor; and a wire configured to connect the insertion bodies along the middle portion.

In some example embodiments, each of the first contactor and the second contactor includes a groove having a shape such that a depth of the groove is deepest at a center and decreases toward ends thereof, and the insertion bodies are configured to penetrate the grooves.

In some example embodiments, when the contactors associated with a first side of the joint assembly are pushed by an external force, a distance between the first contactor and the second contactor on a second side of the joint assembly is increased.

In some example embodiments, the insertion body is configured to move toward the center of the groove to increase the distance between the first contactor and the second contactor.

Some example embodiments relate to a joint assembly.

In some example embodiments, the joint assembly includes a plurality of stacked links having a power transmission cable penetrating therethrough, the plurality of stacked links configured to perform a rolling motion in response to a driving force applied to the power transmission cable.

In some example embodiments, each of the plurality of stacked links has a horseshoe shape configured to wrap around an ankle of a user.

In some example embodiments, ends of each of the plurality of stacked links include a plurality of teeth therein integrally forming a first contactor, and a second contactor connected thereto via a hinge.

In some example embodiments, the first contactor of a first one of the plurality of stacked links is configured to engage the second contactor of a second one of the plurality of stacked links adjacent to the first one of the plurality of stacked links.

In some example embodiments, the ends of the plurality of stacked links have a respective one of a first and second support cables penetrating the first contactor and the second contactor thereat.

In some example embodiments, the first contactor on each of the ends of the plurality of stacked links have first grooves therein facing second grooves associated with the second contactor connected thereto via the hinge.

In some example embodiments, the joint assembly further includes a guide cable having a first wedge and a second wedge connected via a wire, the first wedge configured to sit in a respective one of the first grooves and the second grooves associated with a first end of the plurality of stacked links, and the second wedge configured to sit in a respective one of the first grooves and the second grooves associated with a second end of the plurality of stacked links.

In some example embodiments, the first wedge and the second wedge are configured to generate an elastic force to compensate for misalignment between the plurality of stacked links.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
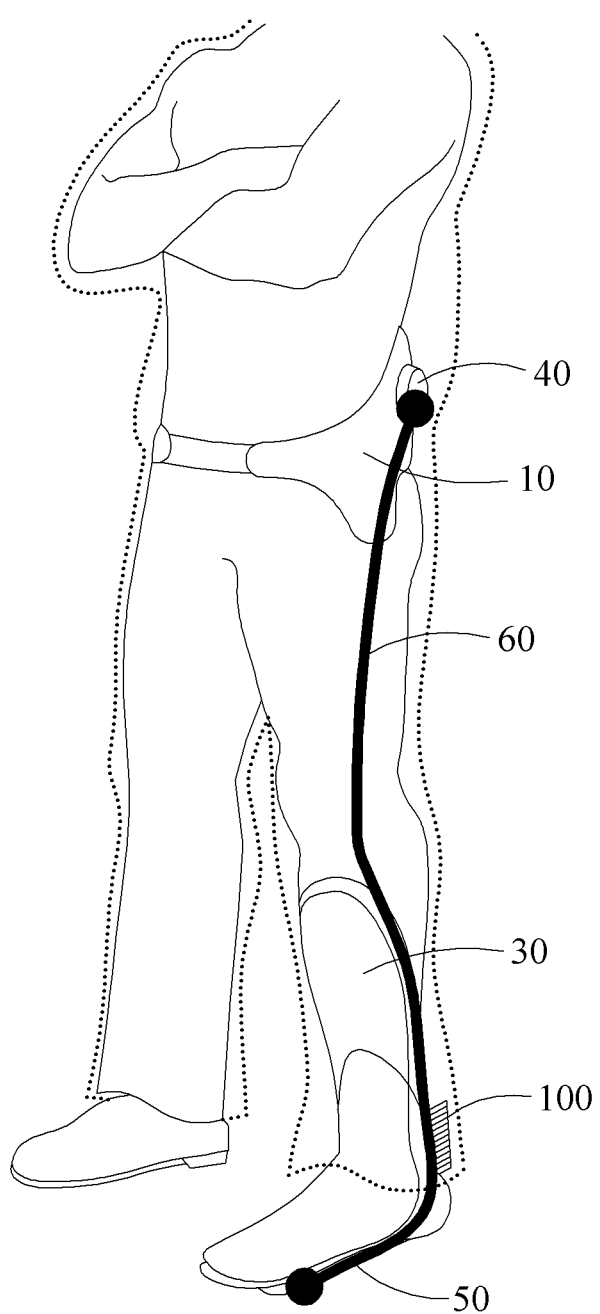
FIG. 1 illustrates an example of a motion assistance apparatus worn by a user.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as one computer processing device; however, one skilled in the art will appreciate that a hardware device may include multiple processing elements and multiple types of processing elements. For example, a hardware device may include multiple processors or a processor and a controller. In addition, other processing configurations are possible, such as parallel processors.

Various example embodiments will now be described more fully with reference to the accompanying drawings in which some example embodiments are shown. In the drawings, the thicknesses of layers and regions are exaggerated for clarity.

Figure 2A:
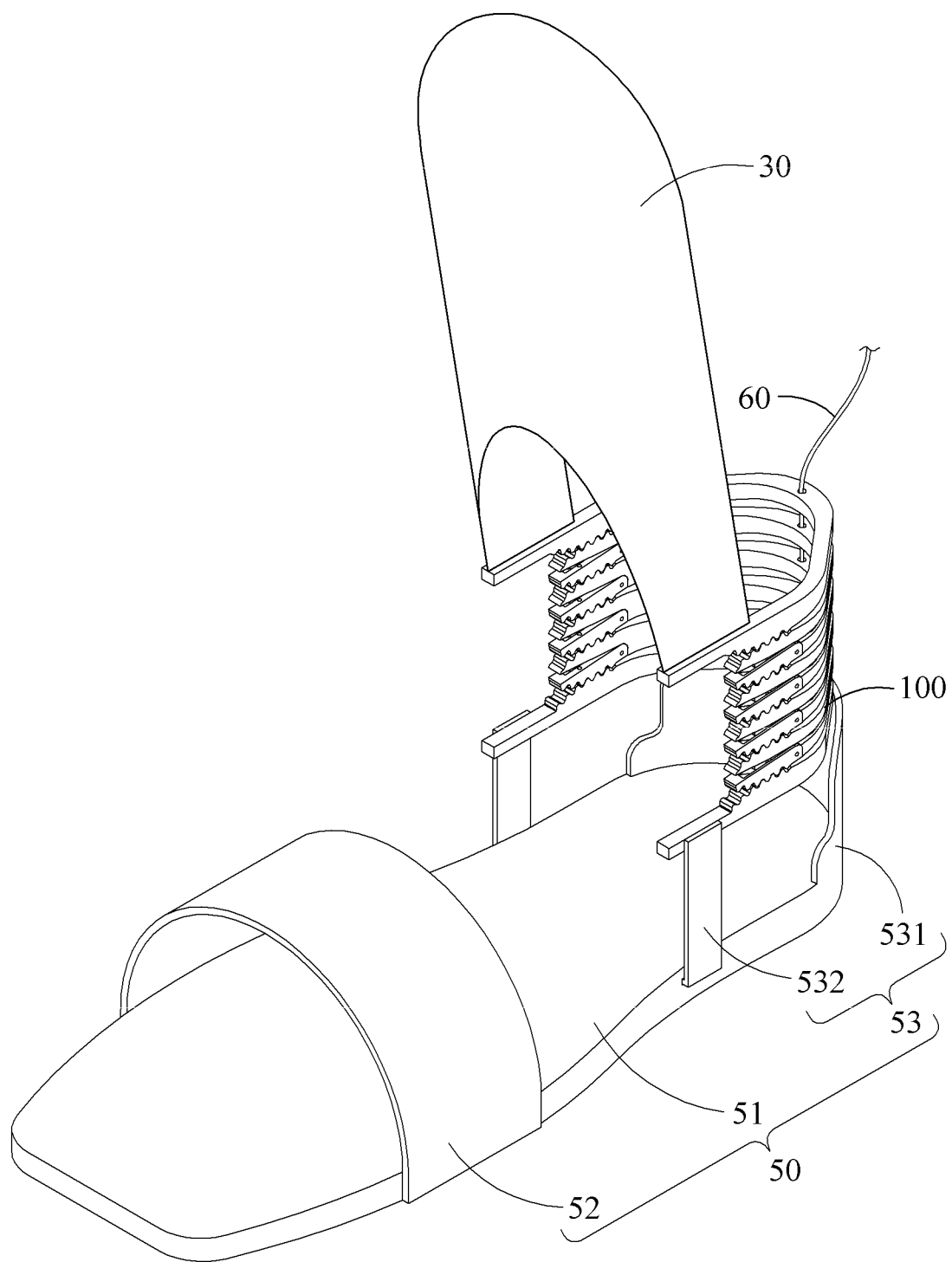
FIG. 2A is a perspective view illustrating an example of a motion assistance apparatus.
Figure 2B:
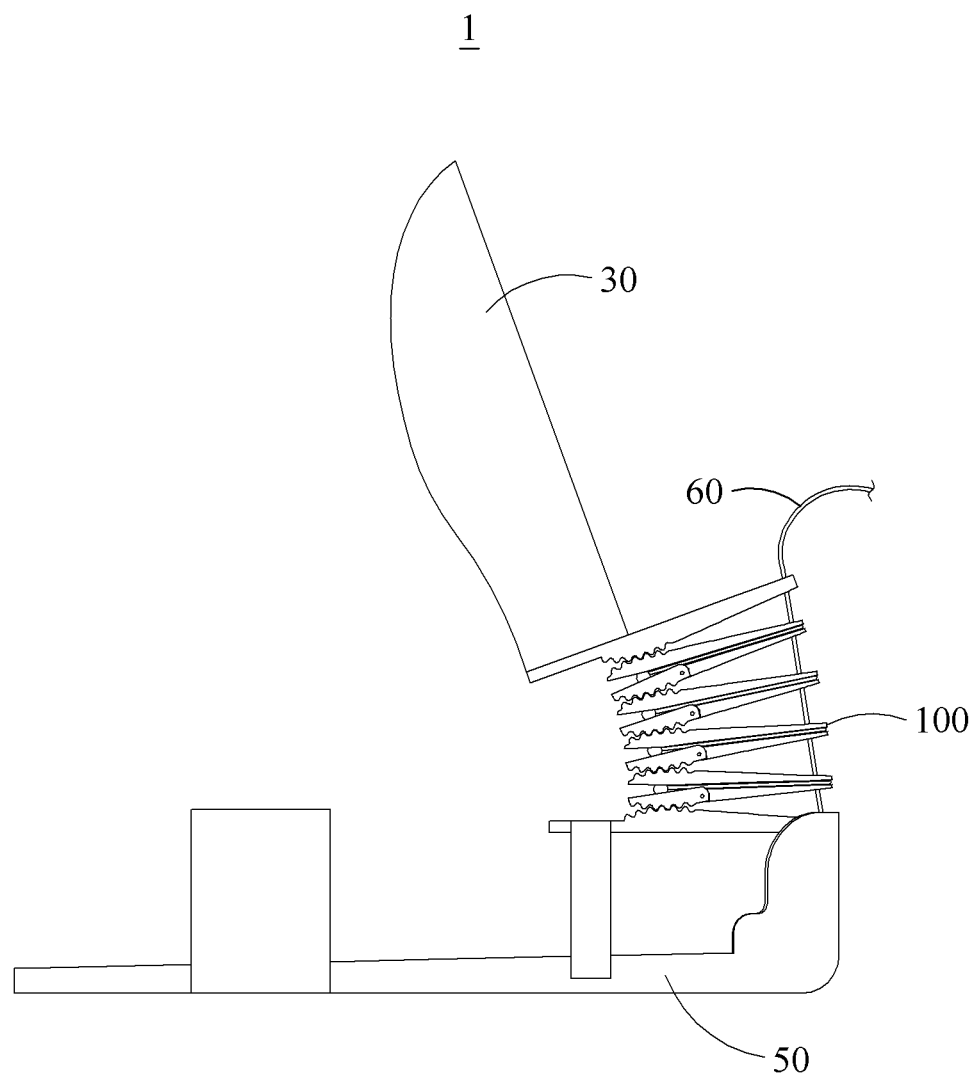
FIG. 2B is a side view illustrating an example of a motion assistance apparatus.

FIG. 1 is a perspective view illustrating a motion assistance apparatus, FIG. 2A is a perspective view illustrating the motion assistance apparatus, and FIG. 2B is a side view illustrating the motion assistance apparatus.

Referring to FIGS. 1 through 2B, a motion assistance apparatus 1 may be worn by a user in order to assist a motion of the user. The user may be a human, an animal, a robot or any other moving structure or being. However, example embodiments are not limited thereto. Further, although FIG. 1 illustrates a case in which the motion assistance apparatus 1 assists a motion of an ankle joint of the user, the motion assistance apparatus 1 may assist a motion of another part, for example, a wrist joint, an elbow joint, and a knee joint of the user. Concisely, the motion assistance apparatus 1 may assist a motion of a part of the user. Hereinafter, a case in which the motion assistance apparatus 1 assists a motion of an ankle joint of a human will be described as an example.

The motion assistance apparatus 1 may include a waist-worn portion 10, a fixing module 30, a driving module 40, a supporting module 50, and a power transmitting member 60, and a joint assembly 100.

Referring to FIGS. 2A and 2B, the fixing module 30 may be attached to a first part of the user, and formed to cover an external surface of the user. For example, the fixing module 30 may be formed to cover a shin of the user, and may include a curved surface corresponding to a contact portion of the user.

The supporting module 50 may be configured to support a second part neighboring the first part of the user, and may rotate relative to the fixing module 30 using power received from the power transmitting member 60. The supporting module 50 may cover a portion of, for example, a bottom or a top of a foot, and an ankle of the user. In an example, the supporting module 50 may include a bottom plate 51 configured to support the bottom of the foot, a foot top supporter 52 configured to support the top of the foot, and a connector 53 configured to connect the bottom plate 51 and the joint assembly 100.

The connecter 53 may include, for example, a heel frame 531 configured to support a heel and a side frame 532 configured to support a side of the foot. A number of connectors 53 and a shape of the connector 53 may not be limited and any form of connecting the joint assembly 100 and the bottom board 51 is applicable to the connector 53. As an example, a portion of the bottom plate 51 may be integrally formed with the joint assembly. In this example, the portion of the bottom plate 51 may be understood as the connector 53.

The side frame 532 may be in a form perpendicular to the bottom plate 51. The side frame 532 may be disposed on a side surface of the bottom plate 51 to connect a portion of an upper end of the side surface and a portion of a lower end of a side surface of the joint assembly 100. The heel frame 531 may be in a form of the heel of the user and a form covering a portion of an Achilles tendon. The heel frame 531 may be configured to connect an upper end of a tail portion of the bottom plate 51 and a lower end of a middle portion of the joint assembly 100.

The driving module 40 may provide power to be transmitted to the supporting module 50 based on instructions received from a controller (not shown).

The controller may include a memory and a processor.

The memory may be a non-volatile memory, a volatile memory, a hard disk, an optical disk, and a combination of two or more of the above-mentioned devices. The memory may be a non-transitory computer readable medium. The non-transitory computer-readable media may also be a distributed network, so that the program instructions are stored and executed in a distributed fashion. The non-volatile memory may be a Read Only Memory (ROM), a Programmable Read Only Memory (PROM), an Erasable Programmable Read Only Memory (EPROM), or a flash memory. The volatile memory may be a Random Access Memory (RAM).

The processor may be implemented by at least one semiconductor chip disposed on a printed circuit board. The processor may be an arithmetic logic unit, a digital signal processor, a microcomputer, a field programmable array, a programmable logic unit, a microprocessor or any other device capable of responding to and executing instructions in a defined manner.

The processor may be programmed with instructions that configure the processor into a special purpose computer to control the driving module 40 based on information from, for example, one or more sensors (not shown).

The driving module 40 may include a clutch module configured to change a velocity, a torque, or a moving direction of the power transmitting member 60. The driving module may be mounted on a position corresponding to a proximal part of the user. The proximal part may be understood as a middle part of a body, for example, a back, a waist, and a trunk of the user. In an example, the driving module 40 may be disposed on the waist-worn portion 10 as illustrated in FIG. 1. In this example, when compared to an example in which the driving module 40 is attached to an end portion of the body, for example, a hand and a foot of the user, energy consumption of the user due to a weight of the driving module 40 may be reduced. In another example, the driving module 40 may be disposed on the fixing module 30 and thus, a position of the driving module 40 is not limited in example embodiments.

The power transmitting member 60 may be configured to transmit power from the driving module 40 to the supporting module 50. The power transmitting member 60 may penetrate the joint assembly 100 to be connected with the supporting module 50. The power transmitting module 60 may include a rotary body such as, for example, a gear or the like, or a longitudinal member such as, for example, a wire, a cable, a string, a rubber band, a spring, a belt, a chain, and the like. The power transmitting member 60 may be wound or unwound by the driving module 40.

The joint assembly 100 may assist a motion of a joint connecting the first part of the user and the second part of the user, for example, the ankle joint of the user. The joint assembly 100 may be connected with the driving module 40 using the power transmitting member 60. The joint assembly 100 may assist a motion of stretching the ankle when the power transmitting member moves upward by the driving module 40 and a motion of bending the ankle when the power transmitting member 60 moves downward.

Figure 3:
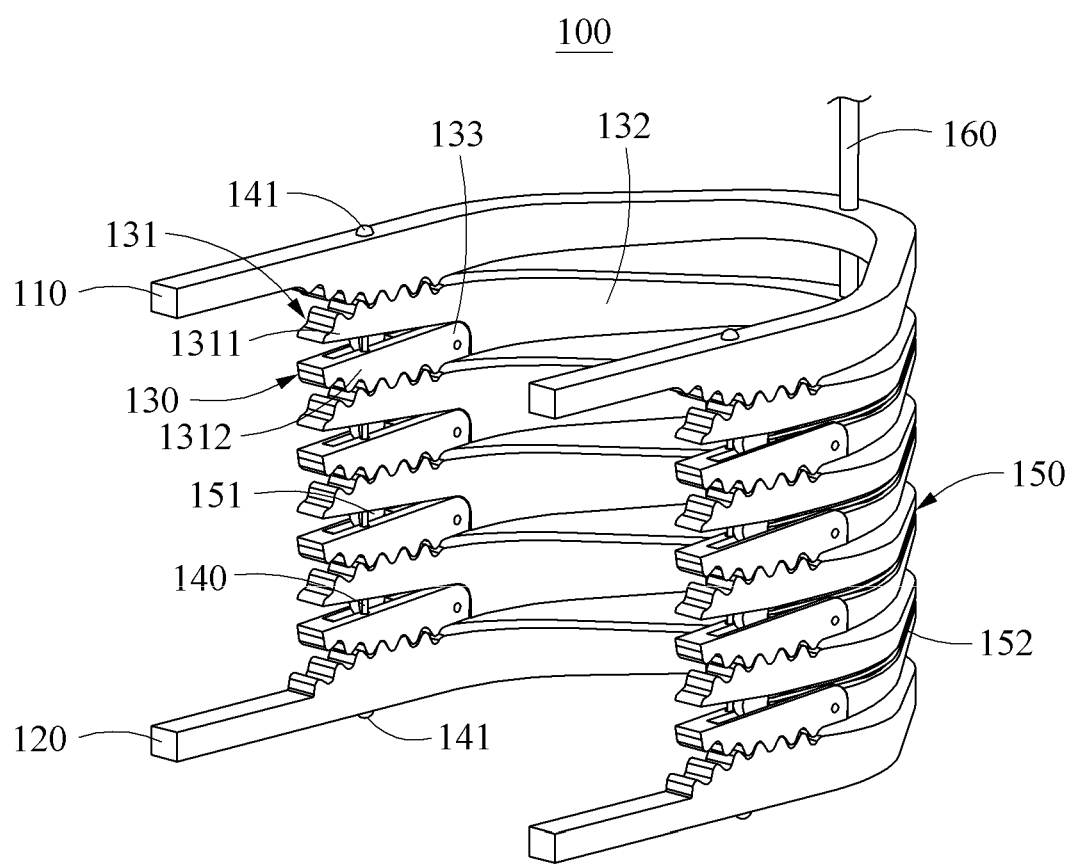
FIG. 3 is a frontal perspective view illustrating an example of a joint assembly.
Figure 4:
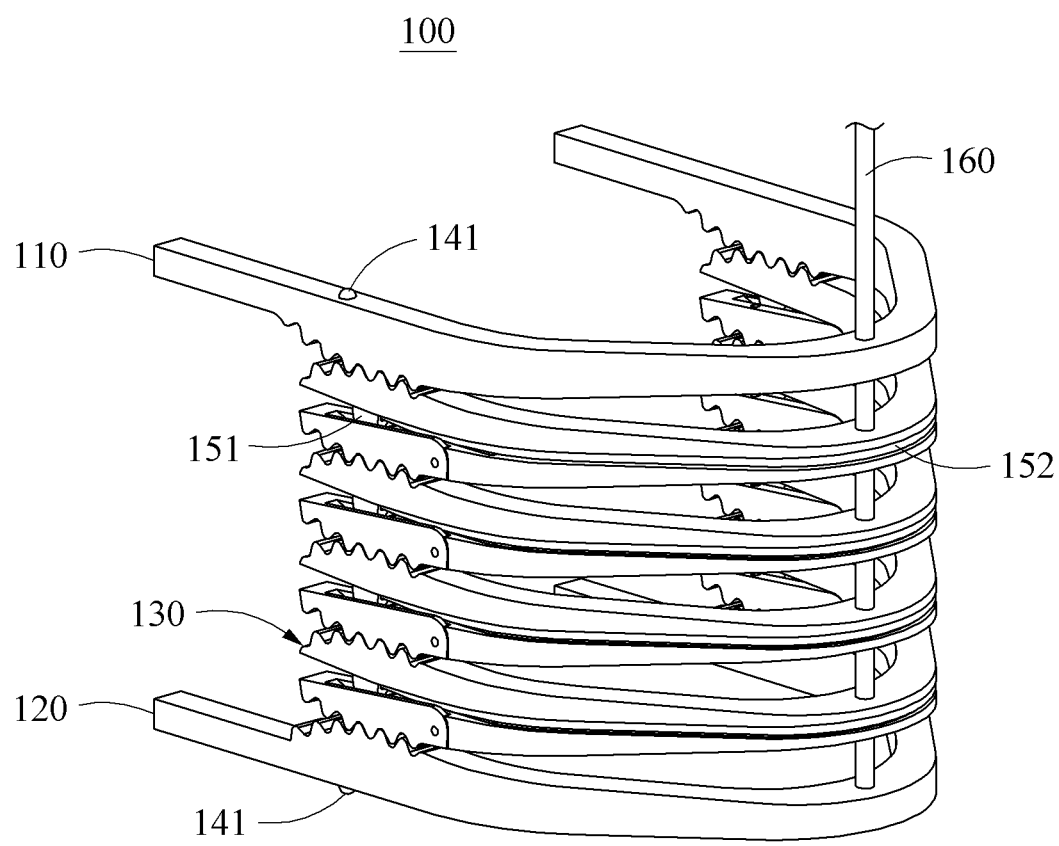
FIG. 4 is a rear perspective view illustrating an example of a joint assembly.

FIG. 3 is a frontal perspective view illustrating the joint assembly 100, and FIG. 4 is a rear perspective view illustrating the joint assembly 100.

Referring to FIGS. 3 and 4, the joint assembly 100 may be provided in a multi-joint link mechanism structure in which a plurality of frames is connected to one another. The joint assembly 100 may include a cover frame 110, at least one middle frame 130, and a bottom frame 120 that may be arranged in an order from top to bottom. The bottom frame 120 may be connected to the supporting module 50.

A plurality of middle frames 130 may be arranged between the cover frame 110 and the bottom frame 120. According to an increase in the number of the middle frames 130, the joint assembly 100 may be provided with various curvatures so as to be changed based on complex rotations of an ankle of a user. Although FIGS. 3 and 4 illustrate four middle frames 130 arranged in sequence as an example, the number of middle frames 130 may vary based on a size of an ankle of the user and a degree of freedom (DOF) of the joint assembly 100. Also, a movable angle of the joint assembly 100 may vary based on a curvature of a contactor 131 of the middle frame 130 or the number of middle frames 130.

The middle frame 130 may include a middle portion 132 and the contactors 131 disposed on both ends of the middle portion 132. In an example, the middle portion 132 may be formed in a U shape frontally extending from a rear face of the ankle of the user to cover a portion of Achilles heel. Unlike what the example drawings currently show, the middle portion 132 may also be formed in various shapes, for example, a polygonal shape and a hemispherical shape.

FIGS. 3 and 4 illustrate the middle portion 132 provided in a symmetric form based on the ankle as an example, and thus, the middle portion 132 may also be provided in an asymmetric form to correspond to a shape of the ankle. To increase a comfort of the user, a fabric pad for impact absorption may be attached to an inner side face of the middle portion 132.

The contactor 131 may be engaged with another contactor 131 of a neighboring middle frame 130. The contactor 131 may have, for example, a form of gear including a plurality of teeth. The contactor 131 may include a first contactor 1311 and a second contactor 1312. For example, the second contactor 1312 may rotate relative to the first contactor 1311 at a connecting point of the first contactor 1311 and the middle portion 132. At a lower end of the first contactor 1311, a hinge 133 may be provided to connect the second contactor 1312 with the middle portion 132 to be rotatable relative to the middle portion 132.

An insertion member 150 may be disposed between the first contactor 1311 and the second contactor 1312. The insertion member 150 may include insertion bodies 151 to be inserted in both ends of the contactor 131, and a wire 152 configured to connect the insertion bodies 151.

The joint assembly 100 may include a connecting member to prevent the cover frame 110, the plurality of middle frames 130, and the bottom frame 120 from separating from one another. For example, the connecting member may be configured to pass through the cover frame 110, the plurality of middle frames 130, and the bottom frame 120. The connecting member may include a side strip 140 formed of an elastic material and configured to pass through the contactors 131 of the plurality of middle frames 130 to provide a pressure allowing the plurality of middle frames 130 to be in close contact with one another, and a middle strip 160 configured to pass through the middle portion 132 of the plurality of middle frames 130.

The middle strip 160 may be connected to the power transmitting member 60 connected with the driving module 40 of the motion assistance apparatus 1. An end portion of the middle strip 160 may be fixed to the bottom frame 120 or the supporting module 50 of FIG. 1. A remaining portion of the middle strip 160 may be movably attached to the cover frame 110 and the middle frame 130. Based on the aforementioned structure, the bottom frame 120 or the supporting module 50 may rotate relative to the fixing module 30 using power transmitted from the power transmitting member 60. Also, in response to a rotating motion of the bottom frame 120 or the supporting module 50, the joint assembly 100 may operate overall. As an example, the middle strip 160 may be integrally formed with the power transmitting member 60.

The side strip 140 may consistently apply the pressure to the middle frame 130 in an inward direction from outside the middle frame 130. Through this, the side strip 140 may maintain contactors of two neighboring frames among a plurality of frames to be in contact with each other. The side strip 140 may include maintaining caps 141 provided on outer side faces of the cover frame 110 and the bottom frame 120 and configured to maintain a tensed state of the side strip 140.

Figure 5:
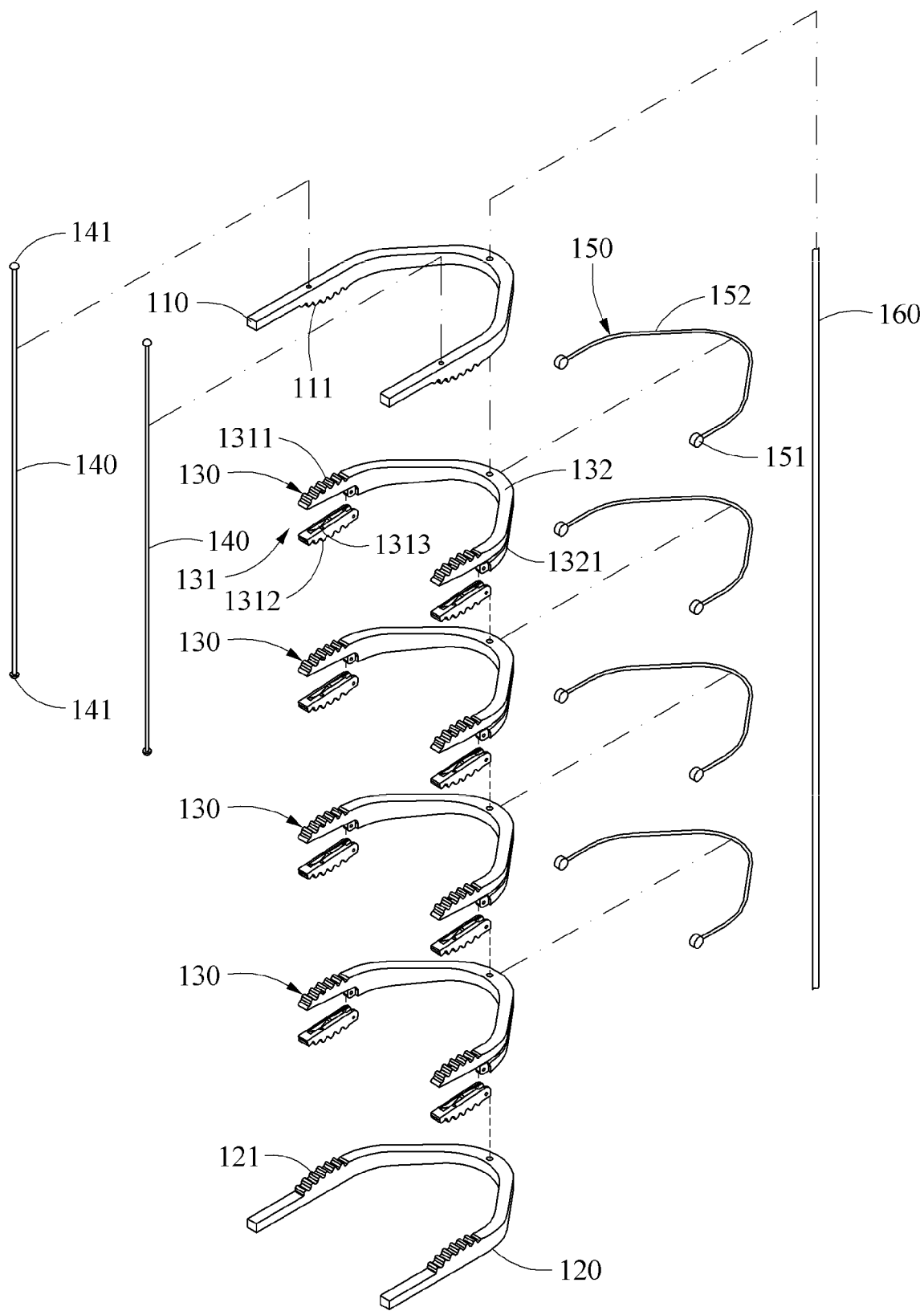
FIG. 5 is a frontal exploded perspective view illustrating an example of a joint assembly.
Figure 6:
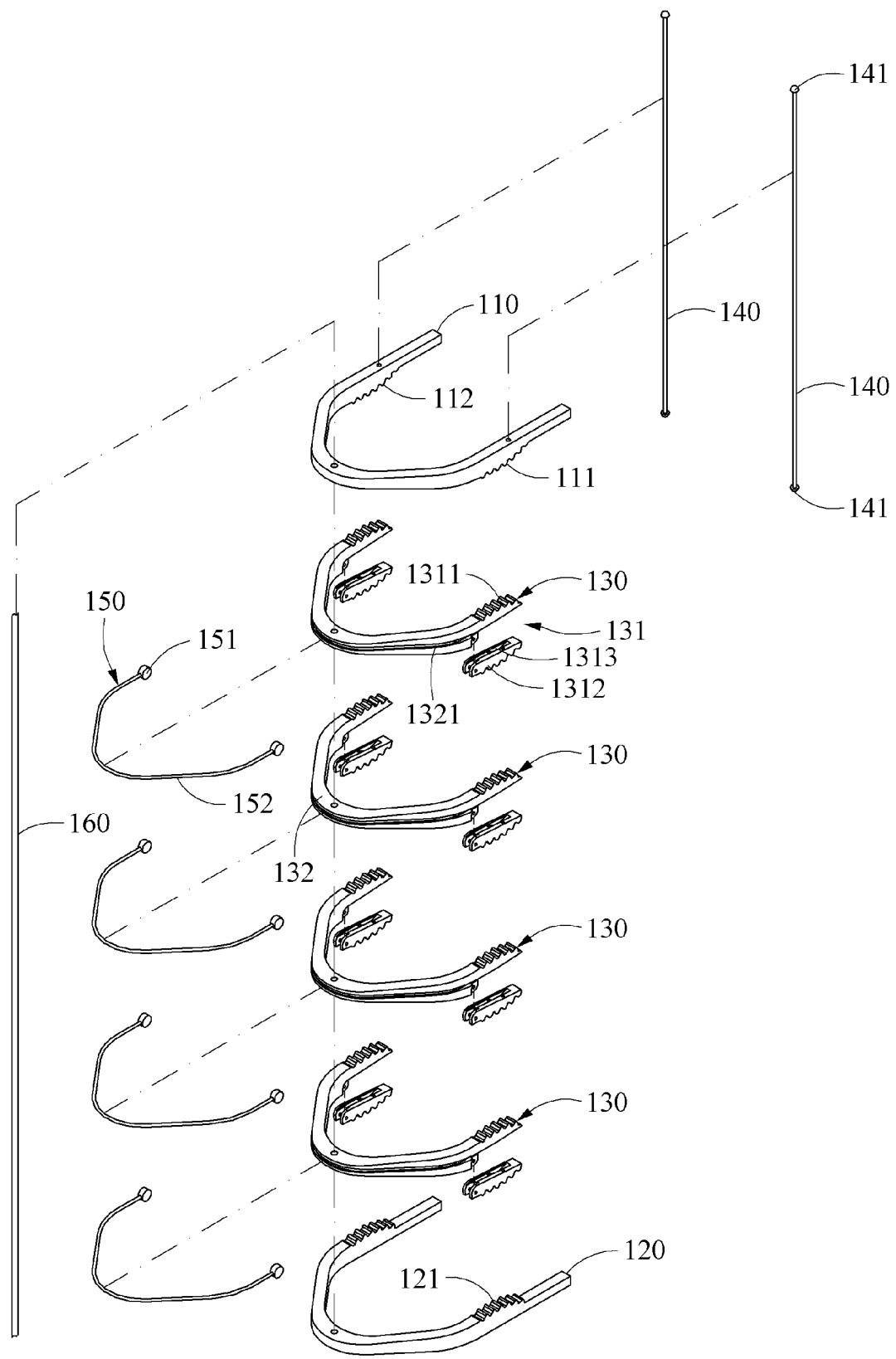
FIG. 6 is a rear exploded perspective view illustrating an example of a joint assembly.

FIG. 5 is a frontal exploded perspective view illustrating the joint assembly 100, and FIG. 6 is a rear exploded perspective view illustrating the joint assembly 100.

Referring to FIGS. 5 and 6, each of the cover frame 110, the bottom frame 120, and the plurality of middle frames 130 arranged in a row may be formed in a U-shape.

The cover frame 110 may include a contacting face 111 on the bottom and the bottom frame 120 may include a contacting face 121 on the top. The contacting faces 111 and 121 may be formed based on a desired (or, alternatively, a preset) curvature. Each of the contacting faces 111 and 121 may have gear teeth repetitively provided in desired (or, alternatively, preset) sizes. The preset curvature may be applied as a base circle of the gear teeth.

Each of the first contactor 1311 and the second contactor 1312 of the middle frame 130 may include a contacting face formed on an outer side face and having a desired (or, alternatively, a preset) curvature. The contacting face may include a gear teeth provided in the same size as that of the contacting face 111 of the cover frame 110. The preset curvature may be applied as a base circle of the gear teeth.

The gear teeth formed on the contacting face 111 of the cover frame 110 and the gear teeth formed on the contacting face of the first contactor 1311 may be engaged with each other, and the gear teeth formed on the contacting face 121 of the bottom frame 120 and the gear teeth formed on the contacting face of the second contactor 1312 may be engaged with each other.

Among the plurality of middle frames 130, the gear teeth of the second contactor 1312 of the middle frame 130 disposed in an upper portion may be engaged with the gear teeth of the first contactor 1311 of the middle frame 130 disposed in a lower portion. As such, the plurality of middle frames 130 may be provided based on a pattern in which gear teeth of the second contactor 1312 of one middle frame 130 are engaged with gear teeth of the first contactor 1311 of another middle frame 130. Thus, a combination of the second contactor 1312 and the first contactor 1311 may be repetitively provided.

A portion of the insertion body 151 of the insertion member 150 may be configured to contact an inner side of the first contactor 1311 of the middle frame 130. Another portion of the insertion body 151 may be configured to contact an inner side of the second contactor 1312. The wire 152 connecting two insertion bodies 151 may be included in a wire guide 1321 formed along an outer side face of the middle portion 132 of the middle frame 130.

Figure 7A:
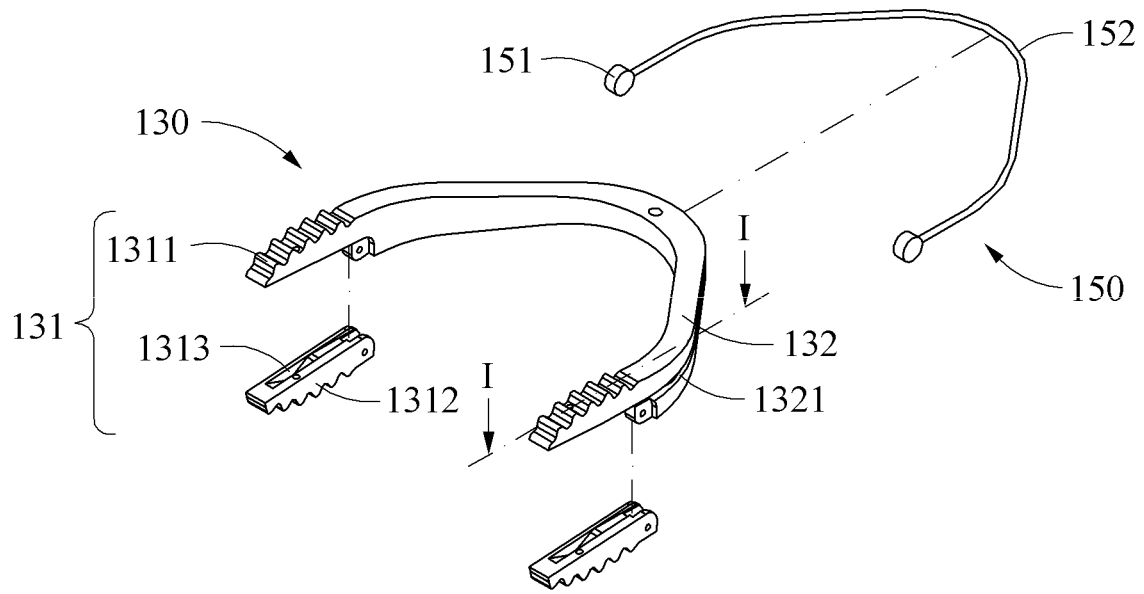
FIGS. 7A through 7C illustrate examples of a middle frame.
Figure 7B:
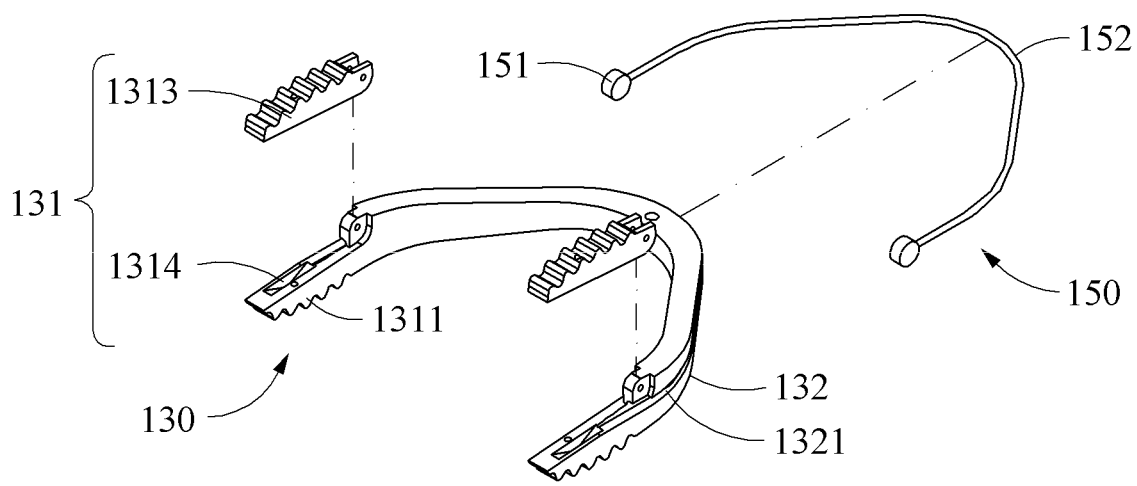
Figure 7C:
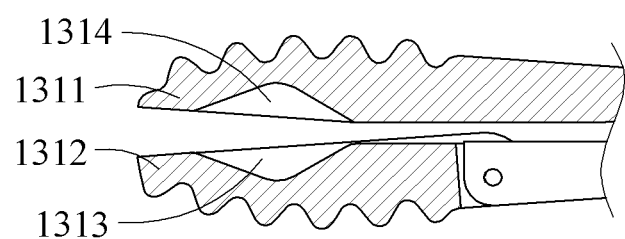

FIGS. 7A through 7C illustrate examples of a middle frame. FIG. 7A is a frontal exploded perspective view illustrating an example of the middle frame 130, FIG. 7B is an exploded perspective view illustrating another example of the middle frame 130, and FIG. 7C is a cross-sectional view illustrating the contactor 131.

Referring to FIGS. 7A through 7C, grooves 1313 and 1314 may be formed on an inner side face of each of the first contactor 1311 and the second contactor 1312. The grooves 1313 and 1314 may be configured to accept the insertion body 151 of the insertion member 150. Each of the grooves 1313 and 1314 may include a middle portion at which a depth is maximized and an end portion in which the depth is decreased from the middle portion toward an end. Each of the grooves 1313 and 1314 may be inwardly recessed to be formed in a wedge-shape.

Referring to FIG. 7C, when the inner side faces of the first contactor 1311 and the second contactor 1312 are in contact with each other, the groove 1313 formed on the second contactor 1312 and the groove 1314 formed on the first contactor 1311 may be in a rhombus shape.

Figure 8A:
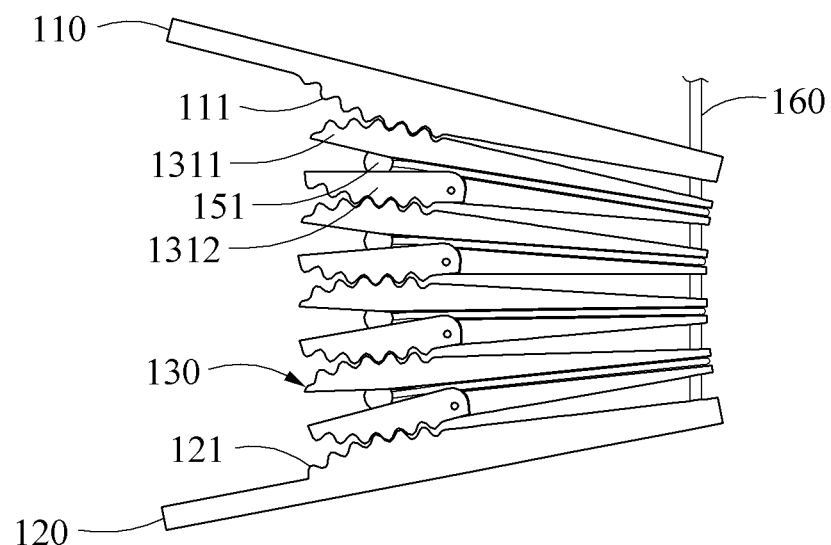
FIG. 8A illustrates an example of a joint assembly operating to assist a planar flexion motion.
Figure 8B:
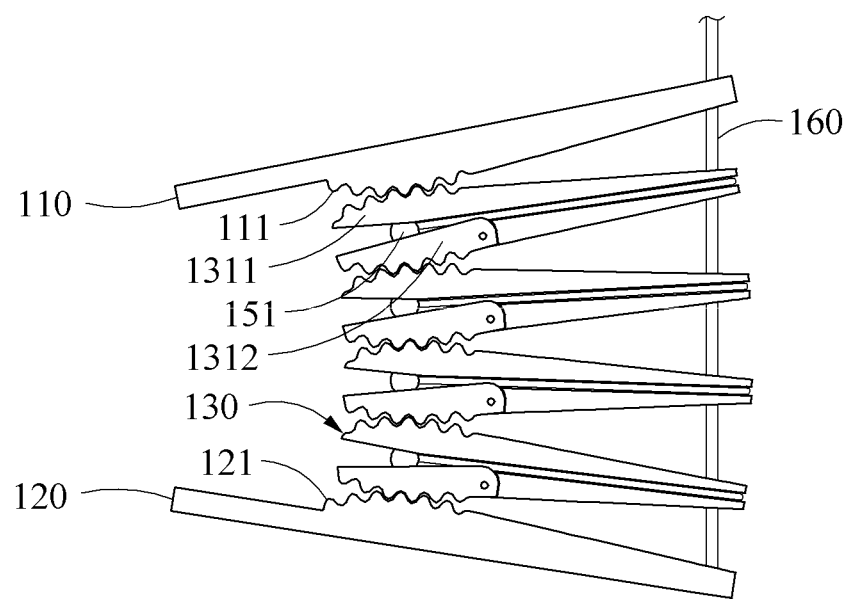
FIG. 8B illustrates an example of a joint assembly operating to assist a dorsiflexion motion.

FIG. 8A illustrates an example of a motion of the joint assembly 100 assisting a plantar flexion motion, and FIG. 8B illustrates a motion of the joint assembly 100 assisting a dorsiflexion motion.

Referring to FIG. 8A, when the middle strip 160 is pulled, the cover frame 110 may rotate relative to the middle frame 130 disposed directly below the cover frame 110 in a clockwise direction and the bottom frame 120 may rotate relative to the middle frame 130 disposed directly above the bottom frame 120 in the counterclockwise direction such that a length of a rear portion of the joint assembly 100 is decreased. Through this, the joint assembly 100 may assist a plantar flexion motion of a user.

Referring to FIG. 8B, when a force of pulling the middle strip 160 is unapplied or a pushing force is applied to the middle strip 160, the cover frame 110 may rotate relative to the middle frame 130 disposed directly below the cover frame 110 in a counterclockwise direction and the bottom frame 120 may rotate relative to the middle frame 130 disposed directly above the bottom frame 120 in the counterclockwise direction such that the length of the rear portion of the joint assembly 100 is increased. Through this, the joint assembly 100 may assist a dorsiflexion motion of the user.

The plurality of middle frames 130 may rotate in a rotation direction of the cover frame 110 and the bottom frame 120. In response to an increase in a distance between the cover frame 110 and the bottom frame 120, the plurality of middle frames 130 may rotate in the counterclockwise direction. In response to a decrease in the distance between the cover frame 110 and the bottom frame 120, the plurality of middle frames 130 may rotate in the clockwise direction.

Frames, for example, the cover frame 110 and the bottom frame 120, the plurality of middle frames 130 may include gear teeth on an outer side face, and the gear teeth may be engaged with each other. Thus, a rolling contact motion may be performed based on a position at which contacting faces of the frames are formed as a rotation axis. Also, the joint assembly 100 may have a plurality of degrees of freedom (DOFs) based on the plurality of middle frames 130 and thus, a center of rotation of the joint assembly 100 may be changed based on a state of ankle. Through this, a misalignment that may occur in a simple hinge-based joint assembly may be prevented.

The frames may perform a seesaw motion based on the contacting faces of the frames. In response to a decrease in a distance between middle portions of the frames, a distance between end portions of the frames may increase. In response to an increase in the distance between the middle portions of the frames, the distance between the end portions of the frames may decrease.

As such, a shape of the joint assembly 100 may be changed in response to the dorisflexion flexion motion or the plantar flexion motion of the user. In this example, a bending angle of the joint assembly 100 may support an overall motion of the ankle of the user and thus, the joint assembly 100 may be smoothly aligned based on an ankle joint of the body. Also, since the frames have the gear teeth engaged with one another, a high intensity of torque may be applied to the joint assembly 100 and the joint assembly 100 may autonomously support a large weight.

FIGS. 9A through 10B illustrate examples of deformation of the joint assembly 100.

A motion of an ankle of a user may include a dorisflexion/plantar flexion motion that the ankle is bent forward or backward, an inversion/eversion motion that a foot is twisted based on a rotation axis extending from a heel to a toe, and a rotation motion based on a shinbone as a rotation axis. Thus, the motion may be taken based on an X axis, a Y axis, and a Z axis.

Figure 9A:
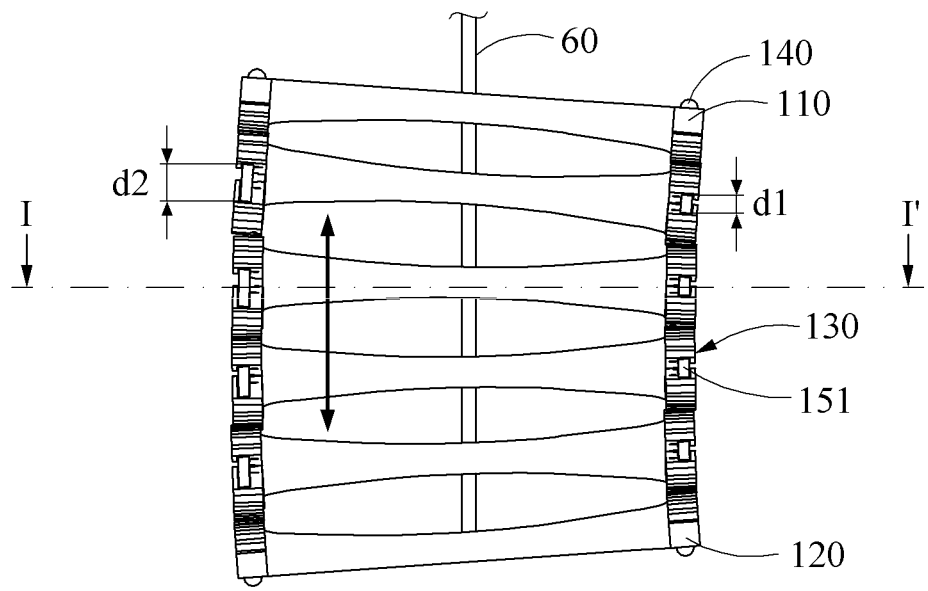
FIGS. 9A through 10B illustrate examples of deformation of a joint assembly.
Figure 9B:
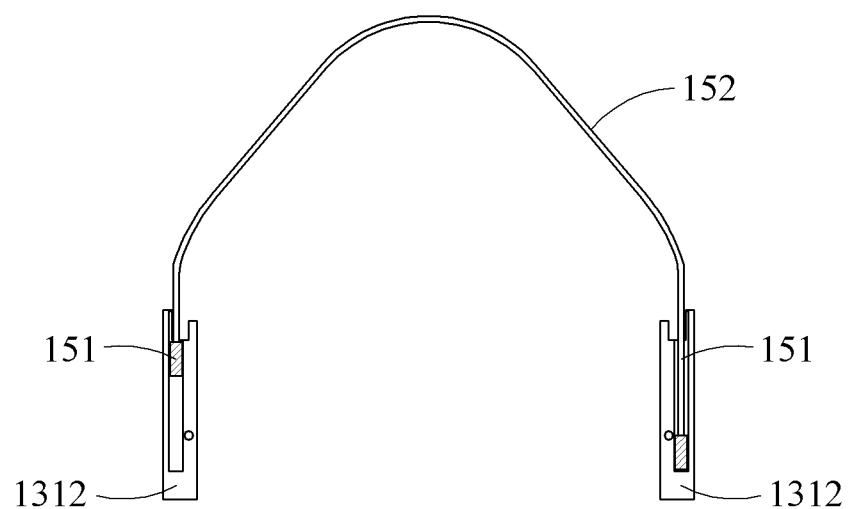

FIGS. 9A and 9B illustrate an example of the joint assembly 100 bent in response to the inversion/eversion motion. FIG. 9A is a frontal view illustrating frames including, for example, the cover frame 110 and the bottom frame 120, the plurality of middle frames 130 when left portions of the frames are separated from one another and right portions of the frames are in contact with one another. FIG. 9B illustrates a movement of the insertion body 151 in an example of FIG. 9A.

When a user wears the joint assembly 100 on a right foot, and when an ankle of the right foot is bent inwardly, the user may be under a circumstance as illustrated in FIGS. 9A and 9B. In this example, a distance d2 between frames disposed adjacent to an outward side of the ankle may increase and a distance d1 between frames disposed adjacent to an inward side of the ankle may decrease.

Conversely, when the user wears the joint assembly 100 on a left foot, and when the ankle of the left foot is sprained outwardly, the user may be under the circumstances as illustrated in FIGS. 9A and 9B. In this example, the distance d2 between the frames disposed adjacent to the inward side of the ankle may increase and the distance b2 between the frames disposed adjacent to the outward side of the ankle may decrease.

The frames may be formed of an inflexible material. For this reason, to trigger the aforementioned movement, the frames may need to be inclined and thus, a misalignment may occur between contacting faces. Separating portions of the frames may form an arc toward non-separating portions of the frame. Simultaneously, the non-separating portions of the frames may also form the arc. The separating portions of the frames may have a length different from a length of the non-separating portions of the frames and form the arc having a concentric.

The insertion body 151 in a left side of the joint assembly 100 is illustrated to be larger than the insertion body 151 in a right side of the joint assembly 100. This is because a portion misaligned from a center in the insertion body 151 on the right may be expressed when a cross-section of the joint assembly 100 is provided based on a center of the insertion body 151 on the left. Such an asymmetric arrangement of the insertion body 151 may be easily understood with reference to FIG. 9B.

Referring to FIG. 9B, the insertion body 151 may asymmetrically move in the groove 1313 formed on the second contacting face 1312 of both sides.

In response to a movement of the insertion body 151 on one side, the insertion body 151 on the other side may move in a direction opposite to the insertion body 151 on the one side through the wire 152. In FIG. 9B, the insertion body 151 on a left may move toward a heel and the insertion body 151 on a right may move toward toes.

Figure 10A:
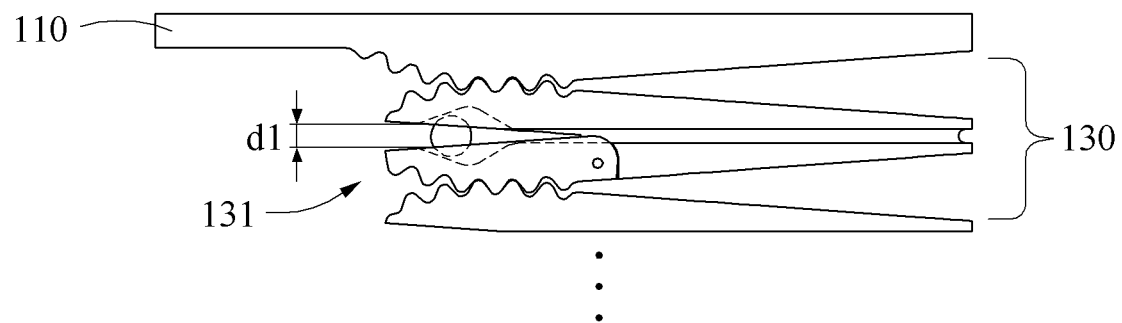
Figure 10B:
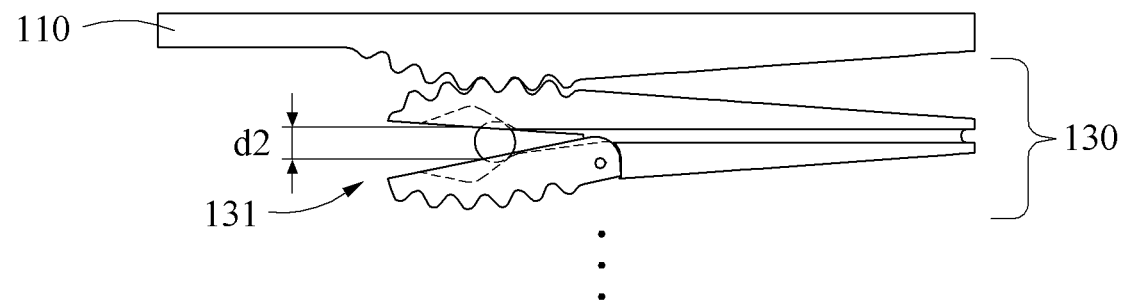

FIG. 10A illustrates the cover frame 110 provided on a right in a flat state or a state of being pushed and the middle frame 130 in contact with the cover frame 110 under the same circumstance as that of FIG. 9. FIG. 10B illustrates the cover frame 110 provided in the right and the middle frame 130 in contact with the cover frame 110 under the same circumstance as that of FIG. 9.

Referring to FIG. 10B, when a right foot is inwardly bent, the insertion body 151 may move along a wire to a portion of the groove 1313 or 1314 of which a depth decreases in a direction of separating frames, for example, the cover frame 110, the bottom frame 120, and the middle frame 130. Through this, the first contacting face 1311 and the second contacting face 1312 may separate from each other and distances separating the frames, for example a distance d2 may increase.

Referring to FIG. 10A, when the insertion body 151 moves in an opposite side of the wire to the other portion of which the depth of the groove 1313 or 1314 decreases, a distance d1 between the first contacting face 1311 and the second contacting face 1312 may not increase. In response to an increase in a length of an ankle joint on one side, a length of the ankle joint on the other side may relatively decrease. In this example, when the length of the ankle joint decreases, an upper end of the frames may be pushed. Thus, a force of the wire pushing the first contacting face 1311 and the second contacting face 1312 may be offset.

Accordingly, the joint assembly 100 may smoothly operate in response to length changes of an inner side and an outer side of an ankle joint based on the foregoing example.

FIGS. 11A through 11D illustrate examples of the joint assembly 100 bent in response to a walking motion of a user. In FIGS. 11A through 11D, an example in which an ankle of the user is twisted in a left or right direction based on toes may be ignored and an example in which the ankle is bent forward or backward may be provided.

Figure 11A:
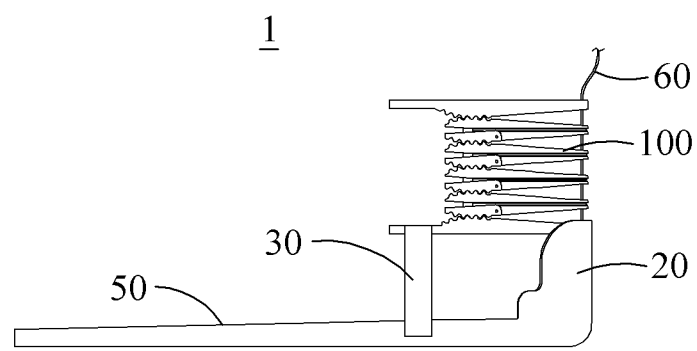
FIGS. 11A through 11D illustrate examples of a motion assistance apparatus including a joint assembly bent in response to a walking motion of a user.
Figure 11B:
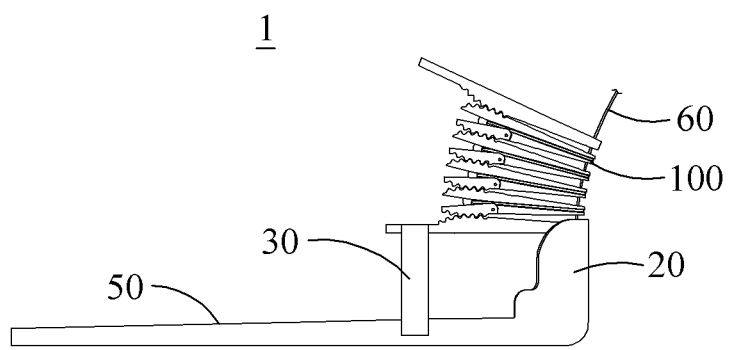
Figure 11C:
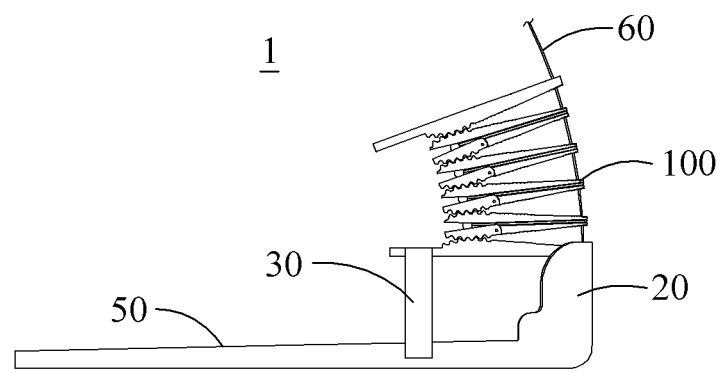
Figure 11D:
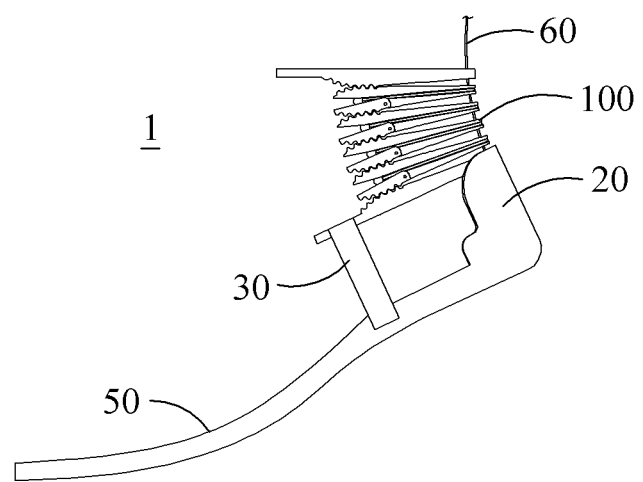

FIG. 11A illustrates an example of the motion assistance apparatus 1 including the joint assembly 100 that is straightened while the user is standing. FIG. 11B illustrates an example of the motion assistance apparatus 1 operating when an ankle is bent backward in response to a motion of a foot stepping forward. FIG. 11C illustrates an example of the motion assistance apparatus 1 operating when the ankle is bent forward such that the stepping foot is rebounded from a ground. FIG. 11D illustrates an example of the motion assistance apparatus 1 operating in response to a take-off motion of the user detaching a foot from the ground.

FIG. 11A illustrates an example in which the cover frame 110, the middle frame 130, and the bottom frame 120 are maintained to be parallel with one another while the user is not moving. In this example, the driving module 40 may not move the power transmitting member 60 upward or downward.

FIG. 11B illustrates an example in which the ankle is bent backward while the user is stepping forward with one leg and standing with the other leg. As illustrated in FIG. 8B, a distance between the middle portions 132 may decrease and a distance between the cover frame 110 and the bottom frame 120 may increase.

FIG. 11C illustrates an example in which the user accumulates energy to apply a force to push the ground after stepping forward. In this example, the ankle may be bent forward. As illustrated in FIG. 8A, the distance between the middle portions 132 may increase and the distance between the cover frame 110 and the bottom frame 120 may decrease.

FIG. 11D illustrates an example in which the foot is rebounded from the ground and the heel is detached from the ground. In this example, the power transmitting member 60 may lift the joint assembly 100. Thus, a portion of the supporting module 50 may be in contact with the ground and the supporting module 50 may be bent. To maintain a body to be balanced, a bottom of the foot may be bent backward and the ankle may be bent in a direction opposite to the bottom of the foot. As illustrated in FIG. 11B, in the joint assembly 100, the distance between the middle portions 132 may decrease and the distance between the cover frame 110 and the bottom frame 120 may increase.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciate that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An exoskeleton joint assembly comprising: a plurality of frames each including a middle portion and contactors, the contactors each including a first contactor and a second contactor, the first contactor being integrally formed on both ends of the middle portion, and the second contactor being movably connected to the first contactor via a hinge, the first contactor and the second contactor each including contacting faces having a plurality of gear teeth therein, the plurality of gear teeth of the first contactor and the plurality of gear teeth of the second contactor facing opposite directions such that the contacting faces of the first contactor and the second contactor are in contact with different ones of two neighboring frames among the plurality of frames; and a connecting member configured to maintain contact between the contactors of the two neighboring frames among the plurality of frames.

2. The exoskeleton joint assembly of claim 1, wherein the contactors associated with a respective one of the plurality of frames face each other with the middle portion of the respective one of the plurality of frames therebetween.

3. The exoskeleton joint assembly of claim 1, wherein the middle portion includes two symmetrically shaped legs extending in a U shape.

4. The exoskeleton joint assembly of claim 1, wherein the contactors include contacting faces, and the two neighboring frames are in contact via the contacting faces.

5. The exoskeleton joint assembly of claim 1, wherein the gear teeth associated with the contacting faces of the two neighboring frames are configured to engage with each other.

6. The exoskeleton joint assembly of claim 1, wherein each of the contactors further includes: an insertion member between the first contactor and each of the second contractors.

7. The exoskeleton joint assembly of claim 6, wherein the insertion member comprises: a plurality of insertion bodies; and a wire configured to connect the insertion bodies along the middle portion of a respective one of the plurality of frames.

8. The exoskeleton joint assembly of claim 7, wherein each of the insertion bodies is configured to contact the inner side face of a respective one of the first contactor and the inner side face of a respective one of the second contactor.

9. The exoskeleton joint assembly of claim 7, wherein each of the first contactor and the second contactor includes a groove to accept a respective one of the insertion bodies.

10. The exoskeleton joint assembly of claim 9, wherein the insertion bodies are configured to longitudinally slide in the groove of a respective one of the contactors.

11. The exoskeleton joint assembly of claim 10, wherein each of the contactors has the groove therein such that a depth of the groove is maximized at a center of a respective one of the contactors and decreases toward both of ends of the respective one of the contactors.

12. The exoskeleton joint assembly of claim 11, wherein when at least one frame of the plurality of frames moves, the at least one frame is configured to move a first one of the plurality of insertion bodies in a first direction and the wire is configured to move a second one of the plurality of insertion bodies in a second direction opposite the first direction.

13. The exoskeleton joint assembly of claim 1, wherein the connecting member further comprises: a side strip configured to pass through the contactors of each of the plurality of frames; and a middle strip configured to pass through the middle portion of each of the plurality of frames.

14. The exoskeleton joint assembly of claim 1, wherein the plurality of frames are configured to align with each other in a longitudinal direction with respect to the connecting member.

15. The exoskeleton joint assembly of claim 1, wherein the connecting member includes an elastic material configured to provide a restoring force to force the plurality of frames back toward in an initial state when the plurality of frames is out of the initial state.

16. The exoskeleton joint assembly of claim 4, further including: a cover frame on top of the plurality of frames and having a contacting face on a bottom thereof; and a bottom frame below the plurality of frames and having a contacting face on a top thereof.

17. A motion assistance apparatus comprising:
a fixing device attached to a user;
a support configured to move relative to the fixing device;
a power transmitting device configured to transmit power to the support; and
a joint assembly including a plurality of frames each including,
a middle portion and contactors, the contactors each including a first contactor and a second contactor, the first contactor being integrally formed on both ends of the middle portion, and the second contactor being movably connected to the first contactor via a hinge, the first contactor and the second contactor each including contacting faces having a plurality of gear teeth therein, the plurality of gear teeth of the first contactor and the plurality of gear teeth of a second contactor facing opposite directions such that the contacting faces of the first contactor and the second contactor are in contact with different ones of two neighboring frames among the plurality of frames, and a connecting member configured to arrange the plurality of frames in a row to connect the fixing device and the support.

18. The motion assistance apparatus of claim 17, wherein the connecting member includes:
a side strip configured to pass through the contactors of each of the plurality of frames, the side strip including an elastic material configured to provide pressure to the plurality of frames such that the plurality of frames is in close contact with one another; and
a middle strip configured to pass through the middle portion of each of the plurality of frames, the middle strip being a wire connected to the power transmitting device.

19. The motion assistance apparatus of claim 17, wherein the plurality of gear teeth of the contactors of the two neighboring frames among the plurality of frames are configured to engage with each other.

20. The motion assistance apparatus of claim 17, wherein the joint assembly further includes a cover frame on top of the plurality of frames and a bottom frame below the plurality of frames, and
each of the contactors further includes an insertion member between the first contactor and the second contactor.

21. The motion assistance apparatus of claim 20, wherein the insertion member includes:
a plurality of insertion bodies each insertable into the first contactor and the second contactor; and
a wire configured to connect the plurality of insertion bodies along the middle portion.

22. The motion assistance apparatus of claim 21, wherein each of the first contactor and the second contactor includes a groove having a shape such that a depth of the groove is deepest at a center and decreases toward both of ends thereof, and
the insertion bodies are configured to be inserted in the groove.

23. The motion assistance apparatus of claim 22, wherein when the contactors associated with a first side of the joint assembly are pushed by an external force, a distance between the first contactor and the second contactor on a second side of the joint assembly is increased.

24. The motion assistance apparatus of claim 23, wherein the insertion bodies are configured to move toward the center of the groove to increase the distance between the first contactor and the second contactor.

25. An exoskeleton joint assembly comprising: a plurality of stacked links having a power transmission cable penetrating therethrough, the plurality of stacked links configured to perform a rolling motion in response to a driving force applied to the power transmission cable, wherein each of the plurality of stacked links has a horseshoe shape configured to wrap around an ankle of a user, and ends of each of the plurality of stacked links include a plurality of teeth therein integrally forming a first contactor, and a second contactor connected thereto via a hinge, the plurality of gear teeth of the first contactor and a plurality of gear teeth of the second contactor facing opposite directions such that contacting faces of the first contactor and the second contactor are each in contact with different ones of two neighboring ones of the plurality of stacked links.

26. The exoskeleton joint assembly of claim 25, wherein the first contactor of a first one of the plurality of stacked links is configured to engage the second contactor of a second one of the plurality of stacked links adjacent to the first one of the plurality of stacked links.

27. The exoskeleton joint assembly of claim 25, wherein the ends of the plurality of stacked links have a respective one of a first and second support cables penetrating the first contactor and the second contactor thereat.

28. The exoskeleton joint assembly of claim 25, wherein the first contactor on each of the ends of the plurality of stacked links have first grooves therein facing second grooves associated with the second contactor connected thereto via the hinge.

29. The exoskeleton joint assembly of claim 28, further comprising: an insertion member having a first wedge and a second wedge connected via a wire, the insertion member having the horseshoe shape such that the first wedge and the second wedge correspond to respective ones of the first contactor, the first wedge configured to sit in the first grooves and the second grooves associated with a first end of the plurality of stacked links, and the second wedge configured to sit in the first grooves and the second grooves associated with a second end of the plurality of stacked links.

30. The exoskeleton joint assembly of claim 29, wherein the first wedge and the second wedge are configured to generate a restoring force to compensate for misalignment between the plurality of stacked links.

* * * * *